(12) United States Patent
Kawamura

(10) Patent No.: US 6,762,054 B2
(45) Date of Patent: Jul. 13, 2004

(54) SOLUTION CONCENTRATION MEASURING METHOD AND SOLUTION CONCENTRATION MEASURING APPARATUS

(75) Inventor: Tatsurou Kawamura, Kyotanabe (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 210 days.

(21) Appl. No.: 09/969,656

(22) Filed: Oct. 4, 2001

(65) Prior Publication Data

US 2002/0042142 A1 Apr. 11, 2002

(30) Foreign Application Priority Data

Oct. 6, 2000 (JP) ....................................... 2000-308144

(51) Int. Cl.[7] .............................................. G01N 21/47
(52) U.S. Cl. ........................ 436/8; 436/164; 422/82.05; 422/82.09
(58) Field of Search .......................... 422/82.05, 82.09; 436/164, 8–19; 356/339, 402, 425, 432, 436, 441, 442

(56) References Cited

U.S. PATENT DOCUMENTS

| | | | |
|---|---|---|---|
| 4,005,983 A | * | 2/1977 | Dahms ........................ 436/42 |
| 4,492,462 A | | 1/1985 | Pross et al. |
| 4,832,488 A | * | 5/1989 | Hirai et al. ............... 356/243.2 |
| 4,884,213 A | * | 11/1989 | Iwata et al. .................... 702/25 |
| 4,983,513 A | | 1/1991 | Lin et al. |
| 5,122,969 A | * | 6/1992 | Seshimoto et al. ........... 702/19 |
| 5,534,441 A | | 7/1996 | Miyazaki et al. |
| 5,554,539 A | * | 9/1996 | Chadney et al. ............... 436/8 |
| 5,565,364 A | * | 10/1996 | Schaefer et al. .............. 436/43 |
| 2002/0138222 A1 | * | 9/2002 | Carpenter et al. .......... 702/104 |

FOREIGN PATENT DOCUMENTS

| | | |
|---|---|---|
| DE | 4441368 A1 | 5/1996 |
| DE | 4441368 A1 | 5/1996 |
| DE | 19629992 A1 | 1/1998 |
| EP | 1096248 A2 | 5/2001 |
| EP | 1113270 A2 | 7/2001 |

* cited by examiner

Primary Examiner—Jeffrey Snay
(74) Attorney, Agent, or Firm—McDermott, Will & Emery

(57) ABSTRACT

In order to improve the reliability of the measurement by judging the precision of a measured value and judging the effectiveness of the measurement based on a result of the precision judgment, the optical characteristic of a reagent solution is previously measured in measuring the concentration of a specific component in a sample solution. Consequently, the precision of the concentration measurement is ensured based on the degree of degradation of the reagent solution.

13 Claims, 11 Drawing Sheets

F I G. 1
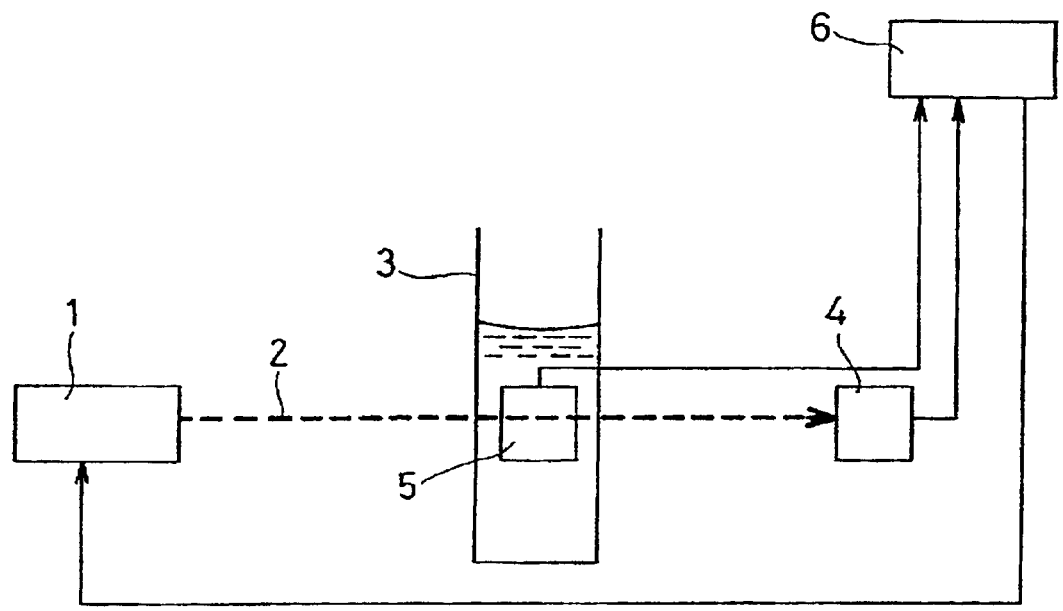
F I G. 2
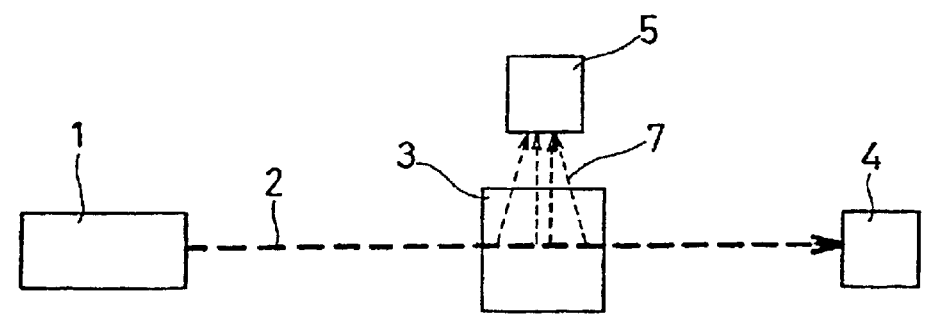

F I G. 3
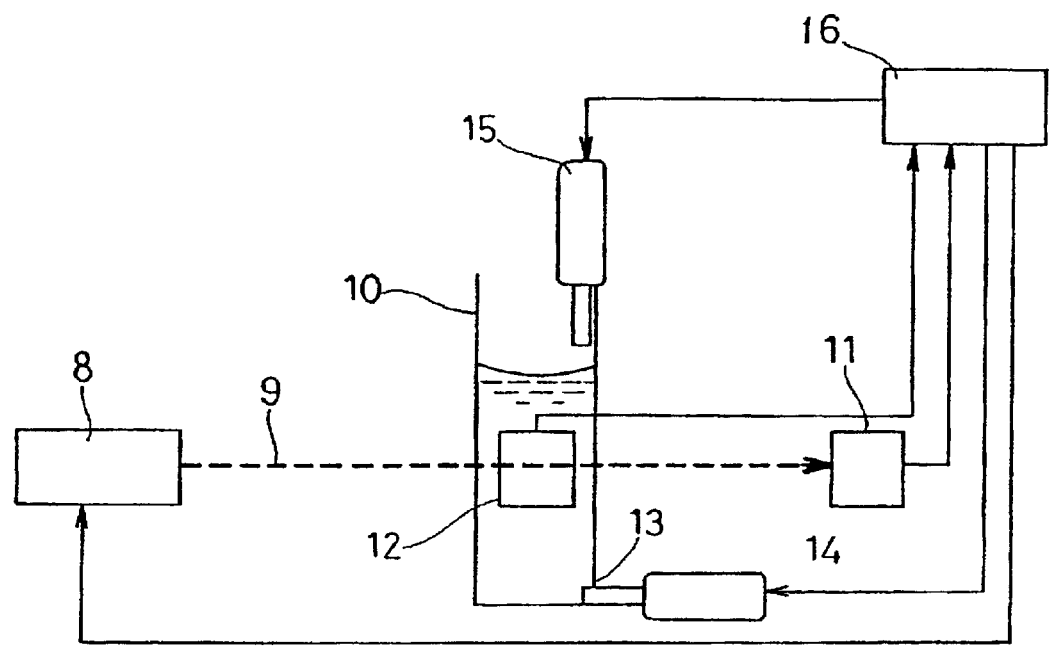
F I G. 4
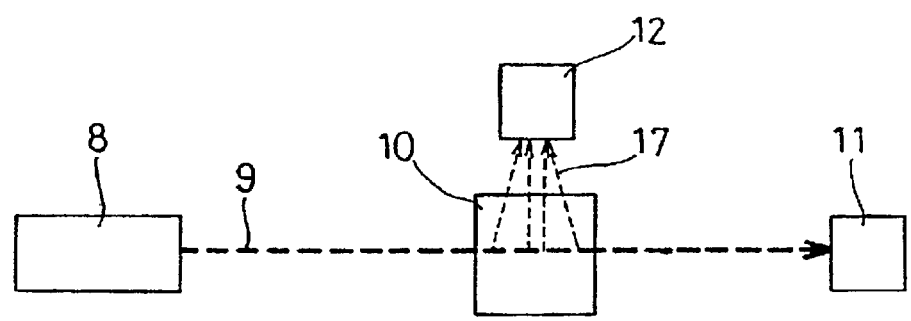

Elapsed time after
mixing antibody reagent solution (second)

Elapsed time after
mixing antibody reagent solution (second)

Storage period of reagent solution (day)

Ratio of turbidity of antibody reagent solution to initial value

F I G. 2 1
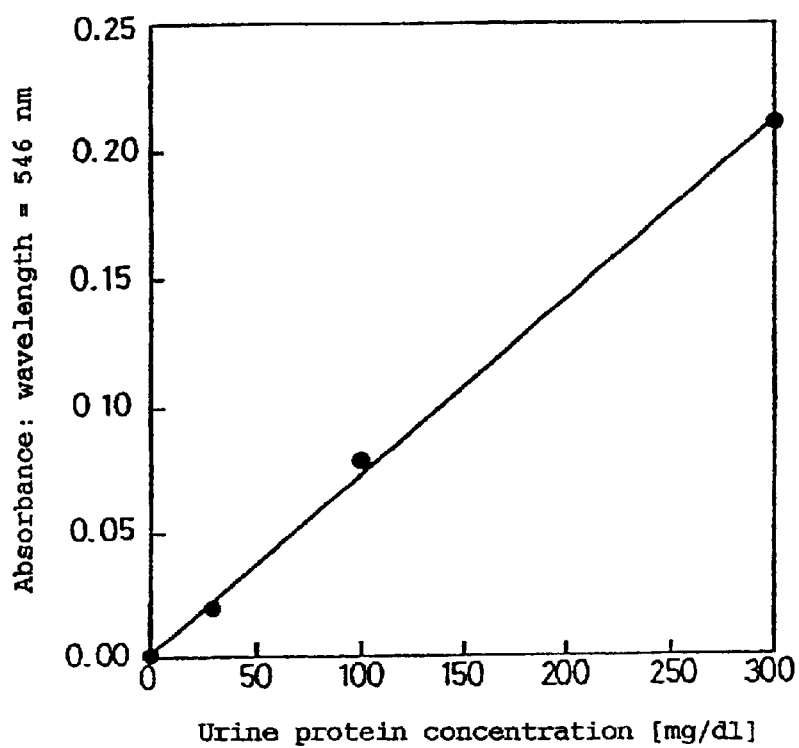

SOLUTION CONCENTRATION MEASURING METHOD AND SOLUTION CONCENTRATION MEASURING APPARATUS

BACKGROUND OF THE INVENTION

The present invention relates to a solution concentration measuring method and a solution concentration measuring apparatus for measuring the concentration of a solute, for example, an optically active substance such as a protein dissolved in a sample solution.

More specifically, the present invention relates to a method and an apparatus for mixing a reagent in a sample solution to change the optical characteristics attributed to a specific component contained in the sample solution, and thereby measuring the concentration of the specific component.

As a solution concentration measuring method adopted in the prior art, there is a coloration method in which a reagent solution containing, for example, a metal ion, a coloring matter or an enzyme is mixed in a sample solution, and allowed to react with a specific component in the sample solution, whereby light absorption characteristic (light absorption spectrum) of the sample solution is changed and the change in the light absorption characteristic is measured by means of a spectroscope or the like.

Further, there is another method in which an acidic reagent solution containing a sulfosalicylic acid or the like is mixed in a sample solution to coagulate the protein in the sample solution, whereby the sample solution is made turbid to measure the turbidity.

Furthermore, there is a still other method in which to an antigen-containing sample solution, a reagent solution containing an antibody against the antigen is mixed to form an antigen-antibody complex, whereby the sample solution is made turbid to detect the reduction in the intensity of a light transmitted through the sample solution, and the increase in the intensity of a scattered light arisen when a light is propagated through the inside of the sample solution, thereby to determine the antigen concentration.

In this case, examples of the antigen when the sample solution is a urine include hemoglobin, albumin, luteinizing hormone and the like. Examples of the antigen when the sample solution is a blood include hemoglobin, saccharified protein, C-reactive protein (CRP) and the like.

On the other hand, as a solution concentration measuring apparatus adopted in the prior art, there is the one using a spectroscope, a liquid chromatograph, or the like. Further, as a urinalysis apparatus, there is a test paper impregnated with a reagent or the like. It is possible to examine a component of a urine by dipping the test paper in the urine, and observing the color reaction thereof by means of a spectroscope or the like. The test papers used herein are individually prepared according to respective inspection items such as glucose and protein.

However, in any of the methods and apparatuses described above, no particular measures have been taken to examine the change in the characteristics of the reagent to be used, and judge the precision of the solution concentration measurement with ease. The reason for this is that the necessity of considering the change in the characteristics of the reagent solution is low in the place where the control system with respect to the expiration date and the storage environment of the reagent solution is established, like a specialized facility such as a hospital.

Further, the person in charge having a technical skill in such a facility carries out the configuration and the functional test of the overall measuring system including a measuring device (spectroscope or the like), if required, by using a standard sample with a known concentration of a specific component (a control urine, a control blood serum, or the like). Therefore, such a countermeasure technology against the change in the characteristics of the reagent that even a layperson not trained can carry out has not been particularly required. Thus, sufficient development thereof has not been done.

However, when a solution concentration measurement examination is carried out at home or the like, there is the following problem. Namely, since there is a wide range of variation in the storage environment comprising temperature, humidity, and sunshine at home, the change in the characteristics of the reagent tends to exhibit a wide range of variation even within a certain period of storage. Particularly, the change in the characteristics of the reagent may exhibit a wide range of variation after opening a container containing the reagent.

Further, those in the ordinary households are not familiar with, and are not trained for the solution concentration measuring method to be applied to the urinalysis or the like. Therefore, the operation of the countermeasure technology against the change in the characteristics of the reagent is desirably as simple as possible, and automated.

Still further, in order for the solution concentration measuring apparatus as described above to come into wide use as a urinalysis apparatus at ordinary households, the apparatus is required to be reduced in size and cost.

In view of the foregoing problems, it is therefore an object of the present invention to provide a solution concentration measuring method whereby the reliability of the measurement is improved by examining the change in the characteristics of a reagent and judging the precision of the measurement, and a solution concentration measuring apparatus, which is compact in size and ensures ease of maintenance and control, usable for such a method.

In other words, it is an object of the present invention to judge the precision of the measurement using a reagent solution by examining the change in the characteristics of the reagent solution when the characteristics of the reagent solution change with time according to the storage environment. Specifically, it is an object of the present invention to provide a method whereby a measurement using a reagent solution is judged as being effective when the change in the characteristics (difference and/or ratio) departs from a predetermined range.

BRIEF SUMMARY OF THE INVENTION

The present invention pertains to a solution concentration measuring method for measuring an optical characteristic of a mixed solution of a sample solution and a reagent solution, and thereby measuring the concentration of a specific component in the sample solution, which comprises the steps of: (1) previously determining a time-varying property A of the optical characteristic of the reagent solution at a time point of storage under a specific storage environment; (2) measuring an optical characteristic of a mixed solution of the sample solution and the reagent solution at the time point of storage to determine a time-varying property B of the optical characteristic of the mixed solution; and (3) judging the precision of a measured value of the concentration of the specific component based on the time-varying properties A and B.

It is effective that the step (3) is a step of forming a characteristic curve showing changes in the optical characteristic of the mixed solution with respect to changes in the optical characteristic of the reagent solution based on the time-varying properties A and B, examining a characteristic of the reagent solution based on the characteristic curve and a measured value obtained by measuring the optical characteristic of the reagent solution, and thereby judging the precision of a measured value of the concentration of the specific component.

It is effective that the optical characteristic of the mixed solution to be measured is an absorbance or a turbidity.

It is effective that the optical characteristic of the reagent solution to be measured is an absorbance or a turbidity.

It is effective that the optical characteristics of the mixed solution and the reagent solution to be measured are the same, and measured by using a light having the same wavelength.

It is effective that the optical characteristics of the mixed solution and the reagent solution to be measured are the same, and measured by means of the same optical characteristic measuring apparatus.

It is effective that the precision of a measured value of the concentration of the specific component is judged to be low when the turbidity of the reagent solution is high or low, and the precision of a measured value of the concentration of the specific component is judged to be high when the turbidity of the reagent solution is low or high.

It is effective that the precision of a measured value of the concentration of the specific component is judged to be high and effective when the turbidity of the reagent solution is not more than or not less than a predetermined value.

It is effective that the precision of a measured value of the concentration of the specific component is judged by taking an absorbance and/or a turbidity of the reagent solution to be used in a first round of the solution concentration measuring method immediately after manufacturing thereof as an initial value, and comparing an absorbance and/or a turbidity of the reagent solution to be used in a second or later round of the solution concentration measuring method is compared with the initial value.

It is effective that the measured value of the concentration of the specific component is judged to be effective when the difference and/or the ratio between the absorbance and/or the turbidity in the second or later round and the initial value is not more than a predetermined value.

The present invention also pertains to a solution concentration measuring apparatus, which comprises: a light source for irradiating a sample solution containing a specific component with a light; a sample cell for holding the sample solution such that a light transmits through the sample solution; a photosensor 1 for detecting the light transmitted through the sample solution and/or a photosensor 2 disposed so as to detect a scattered light arisen when the light propagates through the inside of the sample solution; a transfusion system for introducing the sample solution and a reagent solution into the sample cell; and a computer for controlling the transfusion system to analyze an output signal from the photosensor 1 and/or the photosensor 2, wherein the computer comprises: a memory unit for storing a time-varying property A of an optical characteristic of the reagent solution previously determined a time point of storage under a specific storage environment; a control unit for using an output signal from the photosensor 1 and/or the photosensor 2 as a measured value corresponding to an optical characteristic, and measuring an optical characteristic of a mixed solution of the sample solution and the reagent solution at the time point of storage to determine a time-varying property B of an optical characteristic of the mixed solution; a comparison unit for judging the precision of a measured value of the concentration of the specific component based on the time-varying properties A and B; and a display unit for displaying a result of the precision judgment.

It is effective that the control unit calculates the concentration of the specific component of the sample solution by using an output signal from the photosensor 2 as a measured value corresponding to the optical characteristic when the concentration of the sample solution with a low concentration of the specific component is determined, and using an output signal from the photosensor 1 as a measured value corresponding to the optical characteristic when the concentration of the sample solution with a high concentration of the specific component is determined, thereby to enlarge a measurable concentration range.

Further, it is effective that the control unit improves a characteristic examination precision of the reagent solution by using an output signal from the photosensor 2 as a measured value corresponding to the optical characteristic of the reagent solution.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 1 is a partly sectional schematic side view of a solution concentration measuring apparatus including an optical system and a measurement system, capable of carrying out a method in accordance with the present invention;

FIG. 2 is a schematic top plan view of only the optical system of the solution concentration measuring apparatus shown in FIG. 1;

FIG. 3 is a partly sectional schematic side view of another solution concentration measuring apparatus including an optical system and a measurement system, capable of carrying out a method in accordance with the present invention;

FIG. 4 is a schematic top plan view of only the optical system of the solution concentration measuring apparatus shown in FIG. 3;

FIG. 21 shows a calibration line showing the relation between the protein concentration of a urine and the absorbance of a mixed solution.

DETAILED DESCRIPTION OF THE INVENTION

Figure 5:
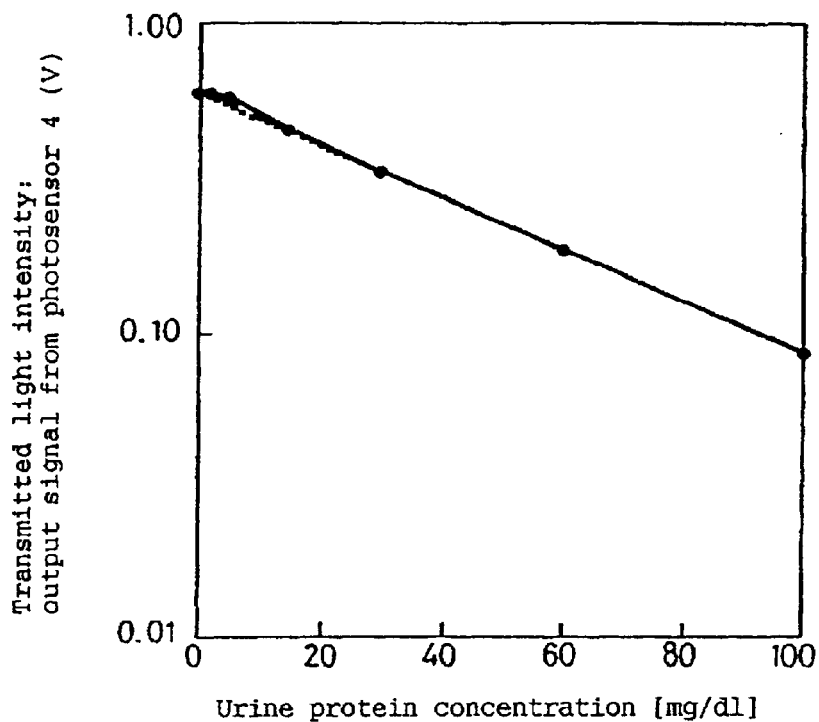
FIG. 5 shows a calibration line showing the relation between the transmitted light intensity and the protein concentration.

As described above, the present invention pertains to a solution concentration measuring method for measuring the concentration of a specific component in a sample solution by measuring the optical characteristics of a mixed solution of the sample solution and a reagent solution, wherein the precision of the measurement using the reagent solution is judged by examining the characteristics of the reagent solution from the measured value obtained by previously measuring the optical characteristics of the reagent solution in measuring the optical characteristics of the mixed solution.

With this method, it is possible to improve the reliability and the precision of the examination, and significantly simplify the examination step. Namely, it is an object of the present invention to judge the precision of the measurement using a reagent solution by examining a time-varying property, i.e., a property changing or deteriorating with the elapse of time, when the characteristics of the reagent solution change with time according to the storage environment.

Although the method of the present invention can be carried out by means of various solution concentration measuring apparatuses, first, a description will be given to one example of a solution concentration measuring apparatus capable of carrying out the method in accordance with the present invention.

FIG. 1 is a partly sectional schematic side view of a solution concentration measuring apparatus including an optical system and a measurement system, capable of carrying out a method in accordance with the present invention. Further, FIG. 2 is a schematic top plan view of only the optical system of the solution concentration measuring apparatus shown in FIG. 1.

In the solution concentration measuring apparatus shown in FIGS. 1 and 2, a light source 1 projects a substantially parallel light 2 having various wavelengths, intensities, and beam diameters. A sample cell 3 has an opening open at the top thereof, and has transparent optical windows each on the respective four sides thereof. The sample cell 3 used herein is so configured that a light can be applied to a sample solution, and a transmitted light and a scattered light can be taken out to the outside while the sample solution is being held therein. Further, there are provided a photosensor 4 for detecting the light transmitted through the sample solution, and a photosensor 5 for detecting a scattered light 7 arisen when the light propagates through the inside of the sample solution. A computer 6 controls the light source 1 to analyze respective output signals from the photosensors 4 and 5.

With this configuration, when the turbidity of the sample solution is increased, the output signal from the photosensor 4 is decreased, and the output signal from the photosensor 5 is increased. Thus, the turbidity can be measured based on the transmitted light intensity or the scattered light intensity.

Further, FIG. 3 shows a partly sectional schematic side view of another solution concentration measuring apparatus including an optical system and a measurement system, capable of carrying out a method in accordance with the present invention. Further, FIG. 4 is a schematic top plan view of only the optical system of the solution concentration measuring apparatus shown in FIG. 3.

The solution concentration measuring apparatus shown in FIGS. 3 and 4 is changed in design from the solution concentration measuring apparatus shown in FIGS. 1 and 2. Therefore, a light source 8, a sample cell 10, a photosensor 11 and a photosensor 12 are the same as the light source 1, the sample cell 3, the photosensor 4, and the photosensor 5, respectively. It is noted that the photosensor 11 detects a substantially parallel light 9, and the photosensor 12 detects a scattered light 17.

In the solution concentration measuring apparatus, an inlet port 13 for injecting a reagent into the sample cell 10 is further provided at the bottom of the sample cell 10. Further, a pipette 14 for introducing a prescribed volume of a reagent solution to a sample solution in the sample cell 10 is disposed, so that a mixed solution of the sample solution and the reagent solution can be prepared in the sample cell 10.

Further, there is disposed a pipette 15 for introducing a prescribed volume of a reagent solution to a sample solution in the sample cell 10 from the opening at the top of the sample cell 10. A computer 16 controls the light source 8 and the pipettes 14 and 15 to analyze respective output signals from the photosensors 11 and 12.

With this configuration, when the turbidity is increased, the output signal from the photosensor 11 is decreased, and the output signal from the photosensor 12 is increased. Thus, the turbidity can be measured based on the transmitted light intensity or the scattered light intensity.

The present inventor has noticed the fact that the measurement precision is influenced by the turbidity of a reagent solution in measuring the concentration of a solution by using the solution concentration measuring apparatus as described above, and has completed the present invention.

A description will be given to the case where the concentration of a urine including a protein as a sample solution is measured by using the solution concentration measuring apparatus shown in FIGS. 1 and 2 or FIGS. 3 and 4.

First, a sulfosalicylic acid reagent solution (a reagent solution obtained by dissolving a salt of sodium sulfate in an aqueous solution of 2-hydroxy-5-sulfobenzoic acid) is mixed in a urine as a sample solution. Then, the protein component is gradually coagulated, so that the mixed solution becomes turbid. The urine is irradiated with light before and after the mixing of the reagent solution, resulting in a reduction in the transmitted light intensity and/or an increase in the scattered light intensity, based on which the protein concentration can be measured.

Further, when a reagent solution obtained by purifying an antibody component from an antihuman rabbit serum albumin is mixed in a urine which is a sample solution, an antigen-antibody complex is formed by the albumin (antigen) and the antibody, so that the sample solution becomes turbid. The urine is irradiated with light before and after the mixing of the reagent solution, resulting in a reduction in the transmitted light intensity and/or an increase in the scattered light intensity, based on which the albumin concentration can be measured.

Thus, by calculating the concentration from the difference between the scattered light intensities before and after the mixing of the reagent solution, it becomes possible to measure the concentration with precision without being affected by the turbidity, the coloration, and the like. Further, by calculating the concentration from the change between the transmitted light intensities before and after the mixing of the reagent solution, i.e., the ratio of the transmitted light intensities before and after the mixing of the reagent solution, it becomes possible to measure the concentration with precision without being affected by the turbidity, the coloration, and the like. Therefore, the foregoing method has a very large practical effect, and enables the improvement of the reliabilities of the measurement and examination.

Herein, if a calibration line showing the relation between the concentration of a protein or an albumin in a urine and the transmitted light intensity or the scattered light intensity is previously formed, it is possible to determine the concentrations only by measuring the transmitted light intensities or the scattered light intensities of various sample solutions.

However, if the characteristics of the reagent solution change between the time when the calibration line has been formed and the time when the concentration of the sample solution is measured, the precision of the measured value of the concentration is fluctuated. For example, if the sulfosalicylic acid reagent solution is allowed to stand at a low temperature, various salts in the sulfosalicylic acid reagent solution precipitate, so that the turbidity of the reagent solution itself may be increased. Whereas, if the reagent solution obtained by purifying an antibody component from an antihuman rabbit serum albumin is allowed to stand at a high temperature for a long time, the turbidity of the reagent solution itself may be increased.

Simultaneously, the turbidity of the mixed solution obtained by mixing any of these turbid reagent solutions with the sample solution may also be changed. However, the changes in the turbidities of these reagent solutions and the mixed solution vary according to the composition of each reagent solution (the kinds of acid, buffer, reaction accelerator, stabilizer, and the like), the kind of the antibody, and the like.

For this reason, in the present invention, when the optical characteristics of a reagent solution change in this manner, the optical characteristics of the reagent solution itself are previously measured, and the precision of the measured value of the concentration, i.e., the effect of the reagent having a changed property on the measurement, is judged by using this measured value.

The optical characteristics of the reagent solution to be used in the present invention, and the time-varying property of the optical characteristics will be described more specifically. As described above, if the reagent solution is allowed to stand for a long time, the optical characteristics such as the absorbance and the turbidity of the reagent solution itself change. For example, a coloring matter or an enzyme is denatured or decomposed, so that the light absorption characteristic (light absorption spectrum) changes, or the metal ions or salt components in the reagent solution precipitate, thereby to increase the turbidity. Whereas, for a reagent solution containing an antibody, the turbidity may be increased by the denaturation or decomposition of the antibody, or the turbidity may also be decreased by precipitations due to the bonds between various additives and the antibody and/or the bonds between various additives, or the like.

The changes in the characteristics of these reagent solutions may be increased under the influences of oxygen, carbon dioxide, or the like after opening a reagent bottle.

The optical characteristics of the sample solution may vary before and after the mixing of the reagent solution due to the changes in the characteristics of each of these reagent solutions. In calculating the concentration of a specific component from the measured optical characteristics of the mixed solution, a calibration line formed by using a reagent solution which has not changed in characteristics is used. Therefore, it can be said that the precision of the measurement using a reagent solution which has changed in characteristics is low.

For this reason, in the present invention, the optical characteristics such as the absorbance and the turbidity of a reagent solution itself are measured, and the precision of the measurement using the reagent solution is judged from the measured value.

The method of the present invention will be described step by step.

1. Step (1)

First, as a step (1), the time-varying property A of the optical characteristics of the reagent solution is determined at each time point of storage under a specific storage environment.

Specifically, the changes with time in the optical characteristics, such as the turbidity and the absorbance of the reagent solution, from immediately after its preparation (or immediately after opening a reagent bottle) are determined. Namely, the wording "the time point of storage" denotes the time elapsed from immediately after manufacturing the reagent solution, or from immediately after opening the reagent bottle. The number of the time points of storage, i.e., the number of measurements of the optical characteristics can be appropriately selected according to the sample solution, the reagent solution, the apparatus configuration, and the like, by any those skilled in the art.

The turbidity and the absorbance of the reagent solution can be detected by measuring the transmitted light intensity and the scattered light intensity. Which is measured may be appropriately selected according to the kind and the characteristics of the reagent solution. However, when the absolute value of the turbidity of the reagent solution is small, the measurement of the turbidity based on the scattered light intensity provides higher sensitivity, and is more advantageous.

Further, the turbidity and the absorbance may be increased with time, or decreased with time.

For example, for the sulfosalicylic acid reagent solution, the turbidity may be increased as the storage period is prolonged. However, if the composition and the storage environment are different, the turbidity may also be decreased due to the precipitation phenomenon of precipitates, or the like as the storage period is prolonged. In such a case, the time-varying property of the turbidity corresponding to the composition, the storage environment, and the like (e.g., FIGS. 7 and 8 described later) is previously measured. Then, a characteristic curve showing the relation between the turbidities of the reagent solution and the mixed solution is determined in a step described later. Based on this, it is possible to judge the precision of the measured value, and judge whether the measurement is effective or ineffective.

Namely, according to the present invention, by previously measuring, and ascertaining the time-varying properties of the turbidities, the optical characteristics, and the like of a reagent solution selected according to the composition of each reagent solution under expected storage environment, and a mixed solution using the same, it is possible to implement the judgment of the precision of the measured value, and the judgment of the effectiveness or the ineffectiveness of the measurement, resulting in an improvement in the reliability of the concentration measurement.

However, the specific storage environment is determined by the ambient temperature, the presence or absence of light, vibration and humidity (particularly after opening), and the like.

2. Step (2)

Next, in a step (2), by mixing a reagent solution at the time point of storage with a sample solution, and measuring the optical characteristics of the mixed solution, the time-varying property B of the optical characteristics of the mixed solution is determined.

Specifically, a reagent solution at each time point of storage is mixed with a sample solution, immediately after acquisition, immediately after preparation, or immediately after opening. The optical characteristics (e.g., transmitted light intensity and scattered light intensity) of the resulting mixed solution are measured.

Namely, a reagent solution after an elapse of a given storage period from immediately after the manufacturing or the opening thereof is used, and mixed with a fresh sample solution to obtain a mixed solution. Then, the optical characteristics of the mixed solution are measured. Therefore, the time-varying property B of the optical characteristics of the mixed solution herein referred to denotes not the time-varying property of the optical characteristics of the mixed solution itself, but the optical characteristics of the mixed solution corresponding to the optical characteristics of the reagent solution at each time point of storage, i.e., the storage period of the reagent solution.

Then, the relation between the storage period of the reagent solution and the optical characteristics of each mixed solution is determined. For example, a calibration line is formed. Further, it is convenient that the optical characteristic of the mixed solution using a reagent solution immediately after its manufacturing is assumed to be 1, which is an initial value, and the optical characteristics of the mixed solution using a reagent solution after an elapse of a certain storage period is indicated as an index. The index may be expressed as either of the difference and the ratio, and it denotes the time-varying property B of the optical characteristics of the mixed solution.

Specifically, the judgment may be carried out based on how many times larger the respective turbidities of the reagent solution and the mixed solution become than the initial value, i.e., based on the ratio between each of the turbidities and the initial value, or the judgment may be carried out based on the difference therebetween. For example, for an initial value of 0.17 V, if it is prescribed that the changes in the scattered light intensity of the mixed solution, i.e., the output signal from a photosensor within a given range (e.g., 0.017 V) relative to the initial value fall with an allowable range, when the scattered light intensity of the reagent solution remains about 1.17 times or less relative to the initial value, it is possible to judge the measurement effective (see FIGS. 13 and 17 described below). Consequently, it is possible to ensure the reliability of the measurement.

Similarly, the turbidity of the reagent solution may also be judged based on the difference between the turbidity and the initial value, i.e., the difference in scattered light intensity.

It is noted that the optical characteristics of the mixed solution and the reagent solution may be individually measured by the same apparatus, or may also be respectively measured by different apparatuses. However, if the measurements are carried out by the same apparatus, advantageously, they are not affected by the variations in the measured value between measuring apparatuses.

Further, if only one kind of optical characteristic (e.g., turbidity) is measured for the reagent solution and the mixed solution, the same measurement system can be advantageously used in the steps (1) and (2). This is because the measurement can be carried out only by means of a turbidity meter for the turbidity, and only by means of an absorbance meter for the absorbance.

Particularly, when the turbidities of the reagent solution and the mixed solution are measured by using a light having the same wavelength, the measurement is very practical because the configuration of a concentration measuring apparatus to be used can be simplified. Of course, even when each absorbance is measured, the measurement by using a light having the same wavelength is similarly advantageous in terms of the apparatus cost.

3. Step (3)

Then, the precision of the measured value of concentration of the specific component is judged based on the time-varying properties A and B.

Specifically, a characteristic curve is formed which shows the changes in the optical characteristics of the mixed solution with respect to the changes in the optical characteristics of the reagent solution based on the time-varying properties A and B of the respective optical characteristics of the reagent solution and the mixed solution.

Namely, for example, a characteristic curve is formed which shows the relation between the optical characteristic of the reagent solution at each time point of storage, i.e., the time-varying property A of the reagent solution, and the optical characteristic of the mixed solution using the reagent solution at each time point of storage, i.e., the time-varying property B of the mixed solution.

Then, the optical characteristic of the reagent solution is examined based on the characteristic curve to judge the precision of the measured value of the concentration.

With the characteristic curve, by determining the optical characteristic of a reagent solution to be used for measuring the concentration of a solution, it is possible to predict the influences of the reagent solution on the optical characteristic of the mixed solution.

Then, if the allowable error range of the measured value of the concentration is previously set based on the characteristic curve according to the storage environment (temperature or the like) of the reagent solution, it is possible to ensure the reliability of the concentration measured value according to the time-varying property of the optical characteristic of the reagent solution.

The method or the apparatus of the present invention is effective for warning of a reduction in the precision of the concentration measurement when the characteristic of the reagent solution is changed as described above. This warning results in an improvement in the reliability of the measurement. Especially when a urine and blood are examined as sample solutions at home or the like, the practicality is high because the method or the apparatus of the present invention is characterized by its easiness, high reliability, compactness, low price, and the like.

Below, the present invention will be described more specifically by way of examples, which should not be construed as limiting the scope of the invention.

EXAMPLE 1

In this example, a method in accordance with the present invention was carried out by using a solution concentration measuring apparatus shown in FIGS. 1 and 2. It is noted that a semiconductor laser module was used as a light source 1, and a substantially parallel light 2 having a wavelength of 780 nm, an intensity of 5.0 mW, and a beam diameter of 2.0 mm was projected therefrom.

First, to a urine judged to have a protein concentration of substantially zero (<0.1 mg/dl), was added a protein to prepare sample solutions with the respective protein concentrations of 0, 2, 5, 15, 30, 60, and 100 mg/dl.

Then, 1 ml of each of the sample solutions was mixed with 1 ml of a sulfosalicylic acid reagent solution (a reagent solution obtained by dissolving a salt of sodium sulfate in an aqueous solution of 2-hydroxy-5-sulfobenzoic acid) to obtain a mixed solution.

In the mixed solution, the protein component was gradually coagulated, so that the mixed solution became turbid. After the degree of turbidity, i.e., the turbidity was stabilized, the mixed solution was introduced into the sample cell 3. The computer 6 operated the light source 1, and at the same time, monitored respective output signals from the photosensors 4 and 5. When the turbidity of the mixed solution was increased, the transmitted light intensity decreased, and the scattered light intensity increased. Therefore, it was possible to measure the protein concentration from the output signals from the photosensors 4 and 5.

Herein, the relation between the measured transmitted light intensity and the protein concentration was shown in FIG. 5. The relation between the scattered light intensity and the protein concentration was shown in FIG. 6. It could also be said that these graphs denote the dependence of the transmitted light intensity or the scattered light intensity on the protein concentration.

Figure 6:
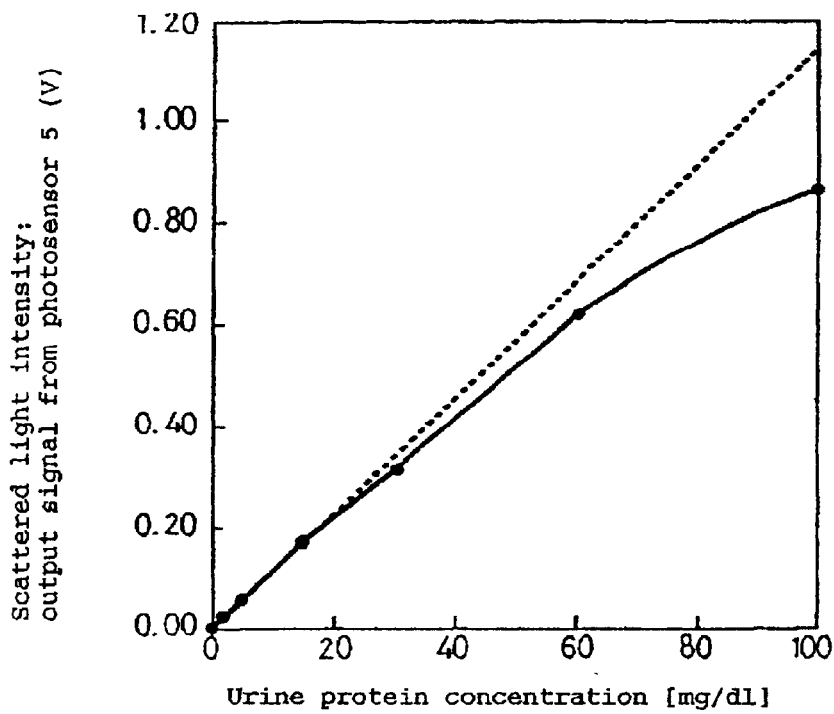
FIG. 6 shows a calibration line showing the relation between the scattered light intensity and the protein concentration.

FIGS. 5 and 6 could be used as calibration lines for concentration measurement. With the conditions under which the calibration lines were formed, and the settings of the measurement system shown in FIGS. 1 and 2, the sample solution and the reagent solution before the mixing were substantially transparent. Namely, the transmitted light intensity and the scattered light intensity (respective output signals from the photosensors 4 and 5) when the sample solution or the reagent solution was charged alone into the sample cell 3, without being mixed, were the same as the transmitted light intensity and the scattered light intensity of pure water, respectively. The scattered light intensity could be substantially regarded as zero.

In FIG. 5, the abscissa denoted the protein concentration, and the ordinate (logarithmic scale) denoted the transmitted light intensity. FIG. 5 indicated as follows: the turbidity was increased with an increase in the protein concentration, and hence the transmitted light intensity, i.e., the output signal from the photosensor 4 decreased.

Respective points were smoothly connected to obtain a solid line, and the points showing linearly changing values at concentrations of 15, 30, 60, and 100 mg/dl were connected to obtain a dotted line.

As shown in FIG. 5, at concentrations of 2 and 5 mg/dl, the transmitted light intensity might deviate from the dotted line. The reason for this was as follows: since the amount of change in the transmitted light intensity as compared with the case where the protein concentration was 0 mg/dl, i.e., the ratio of change was too small as compared with all the output signals, the measured value was susceptible to various noises in association with the dynamic range.

Consequently, when the concentration was calculated from the transmitted light intensity, a high concentration region of 15 mg/dl or more was desirable for avoiding the influences of various noises.

In FIG. 6, the abscissa denoted the protein concentration, and the ordinate denoted the scattered light intensity. FIG. 6 indicated as follows: the turbidity was increased with an increase in the protein concentration, and hence the scattered light intensity, i.e., the output signal from the photosensor 5 increased.

Respective points were smoothly connected to obtain a solid line, and the points showing linearly changing values at concentrations of 0, 2, 5, and 15 mg/dl were connected to obtain a dotted line. As apparent from the solid line and the dotted line, the scattered light intensity was proportional to the concentration at concentrations of up to about 15 mg/dl. However, as the concentration increases more than the value in the vicinity of this range, the gradient was gradually decreased.

The reason for this was as follows. When the probability that light was scattered was increased with an increase in the concentration, the probability that light was scattered again was also increased during propagation of light from the point where the scattered light had arisen to the outside of the sample cell, resulting in a reduction in the probability that the scattered light reached the photosensor 5. Therefore, when the concentration was calculated from the scattered light intensity, the linearity could be ensured only in the low concentration region (about 15 mg/dl or less).

For the low concentration region, the concentration was calculated from the scattered light intensity. Whereas, for the high concentration region, the concentration was calculated from the transmitted light intensity. Consequently, it was possible to enlarge the concentration range measurable with substantially high precision, i.e., the dynamic range. Specifically, it was indicated as follows. When the transmitted light intensity, i.e., the output signal from the photosensor 4 was about 0.4 V or less, it was effective that the concentration was calculated by using the graph of FIG. 5 as a calibration line. Whereas, when the scattered light intensity, i.e., the output signal from the photosensor 5 was about 0.2 V or less, it was effective that the concentration was calculated by using the graph of FIG. 6 as a calibration line.

Herein, if the optical path length was elongated, measurement could be carried out with high precision for the low concentration region even by measuring only the change in the transmitted light intensity. However, in the high concentration region, the absolute value of the transmitted light intensity was decreased, and a noise was increased, resulting in a reduction in precision. Further, there was another problem that an increase in the optical path length results in an increase in the apparatus scale.

In this example, the measurement could be carried out with higher precision based on the scattered light intensity for the low concentration region, and based on the transmitted light intensity for the high concentration region, wherein the low concentration region ranged up to about 15 mg/dl or less, and the high concentration region ranged down to about 15 mg/dl or more. However, the concentration range in each of the low and high concentration regions varied according to the optical length of the sample cell 3, the propagation distance in the sample solution of the scattered light 7, the arrangement of the optical system, and the like, it was not limited to the numerical values described above.

In actuality, when the optical path length of the transmitted light was set to be longer than 10 mm, it was also possible to calculate the concentration with high precision by measuring the transmitted light intensity even when the concentration was 15 mg/dl or less. However, when the optical path length was elongated in this manner, the output signal from the photosensor 4 became too small (about $10^{-4}$ V), and hence it became difficult to determine the concentration. Further, the elongation of the optical path length inevitably enlarged the apparatus scale, and such a large scale apparatus was not preferred from the practical viewpoint.

In short, according to the method as described above, when the structure and the scale of the apparatus were under a certain restriction, by utilizing both the scattered light and the transmitted light, it was possible to enlarge the measurable concentration range, i.e., the dynamic range.

Next, the method of the present invention was carried out with consideration given to the time-varying property of the optical characteristics of a reagent solution.

(1) Step of Determining the Time-varying Property A of the Optical Characteristics of a Reagent Solution at Respective Time Points of Storage Under a Specific Storage Environment First, a sulfosalicylic acid reagent solution (a reagent solution obtained by dissolving a salt of sodium sulfate in an aqueous solution of 2-hydroxy-5-sulfobenzoic acid) was prepared in the same manner as described above.

Subsequently, only the reagent solution was charged into the sample cell 3 of the solution concentration measuring apparatus shown in FIGS. 1 and 2 to measure the turbidity. At this step, the output signal from the photosensor 5 was enlarged (amplified) to 1000 times the signal when the calibration lines shown in FIGS. 5 and 6 had been formed, and observed by the computer 6.

Then, the turbidity of the reagent solution was measured 21 times every 30 days from immediately after the preparation of the reagent solution to 600th days therefrom.

Figure 7:
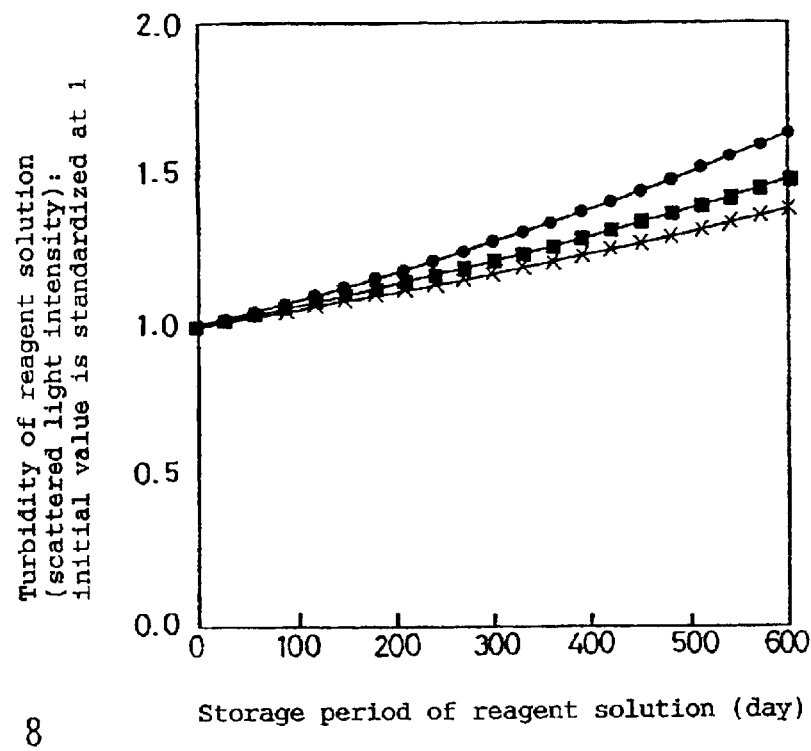
FIG. 7 shows calibration lines each showing the relation between the storage period of a reagent solution and the scattered light intensity of the reagent solution.

The result, i.e., the time-varying property A, was shown in FIG. 7. In FIG. 7, the abscissa denoted the storage period (the number of days elapsed from immediately after the preparation) of the reagent solution. Whereas, the ordinate denoted the scattered light intensity at each time point when the scattered light intensity (output signal from the photosensor 5) immediately after the preparation was assumed to be an initial value. Namely, the initial value was assumed to be 1, and the subsequent scattered light intensities were indicated by indexes. Then, regarding these indexes as turbidities, respective points were smoothly connected by a solid line.

In FIG. 7, the mark "●" indicated the case where the reagent solution stored at about 0° C. was used; the mark "■" indicated the case where the reagent solution stored at about 40° C. was used; and the mark "x" indicated the case where the reagent solution stored at about 8° C. was used. However, in any case, the temperature was raised to room temperature (about 20° C.) for measuring the turbidity.

(2) Step of Measuring the Optical Characteristics of a Mixed Solution at Respective Time Points of Storage, and Determining the Time-varying Property B of the Optical Characteristics of the Mixed Solution Whereas, the scattered light intensity (output signal from the photosensor 5) of a sample solution having a protein concentration of 15 mg/dl was measured by using the reagent solution under the same conditions and settings as those for forming the calibration line shown in FIG. 6.

Namely, the reagent solution after each storage was mixed with the fresh sample solution, and the turbidity, i.e., the scattered light intensity of the resulting mixed solution was measured every 30 days from immediately after the preparation of the reagent solution to 600th days therefrom. However, the sample solution had been prepared immediately before each measurement, and hence no consideration was given to the change in the characteristics of the sample solution itself.

Figure 8:
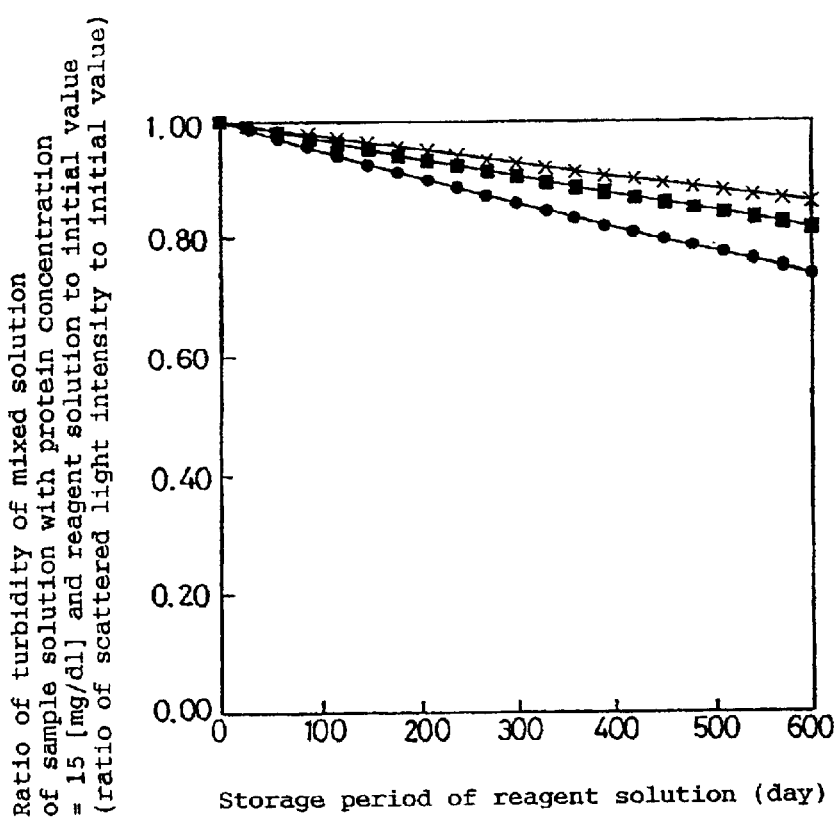
FIG. 8 shows calibration lines each showing the relation between the storage period of a reagent solution and the scattered light intensity of a mixed solution using the reagent solution at each time point of storage.

The result, i.e., the time-varying property B, was shown in FIG. 8. In FIG. 8, the abscissa denoted the storage period (the number of days elapsed from immediately after the preparation) of the reagent solution. Whereas, the ordinate denoted the scattered light intensity of the mixed solution using the reagent solution at each time point of storage, on the assumption that the scattered light intensity (output signal from the photosensor 5) of the mixed solution measured by using the reagent solution immediately after the preparation was an initial value. Namely, the scattered light intensities were indicated by indexes with the initial value being set to be 1. Then, respective points were smoothly connected by a solid line.

In FIG. 8, the mark "●" indicated the turbidity of the mixed solution using the reagent solution stored at about 0° C.; the mark "■" indicated the turbidity of the mixed solution using the reagent solution stored at about 4° C.; and the mark "x" indicated the turbidity of the mixed solution using the reagent solution stored at about 8° C. However, in any case, the temperature was raised to room temperature (about 20° C.) for measuring the turbidity.

As apparent from FIG. 7, the turbidity of the reagent solution was increased with an increase in the storage period. For example, the scattered light intensity of the reagent solution stored at about 0° C. indicated by the mark "●" was about 1.18 times the initial value after an elapse of 200 days, and about 1.65 times the initial value after an elapse of 600 days.

Whereas, as apparent from FIG. 8, the turbidity of the mixed solution of the sample solution and the reagent solution was decreased with an increase in the storage period. For example, the turbidity of the mixed solution using the reagent solution stored at about 0° C. indicated by the mark "●" was about 0.9 times the initial value after an elapse of 200 days, and about 0.74 times the initial value after an elapse of 600 days.

Figure 9:
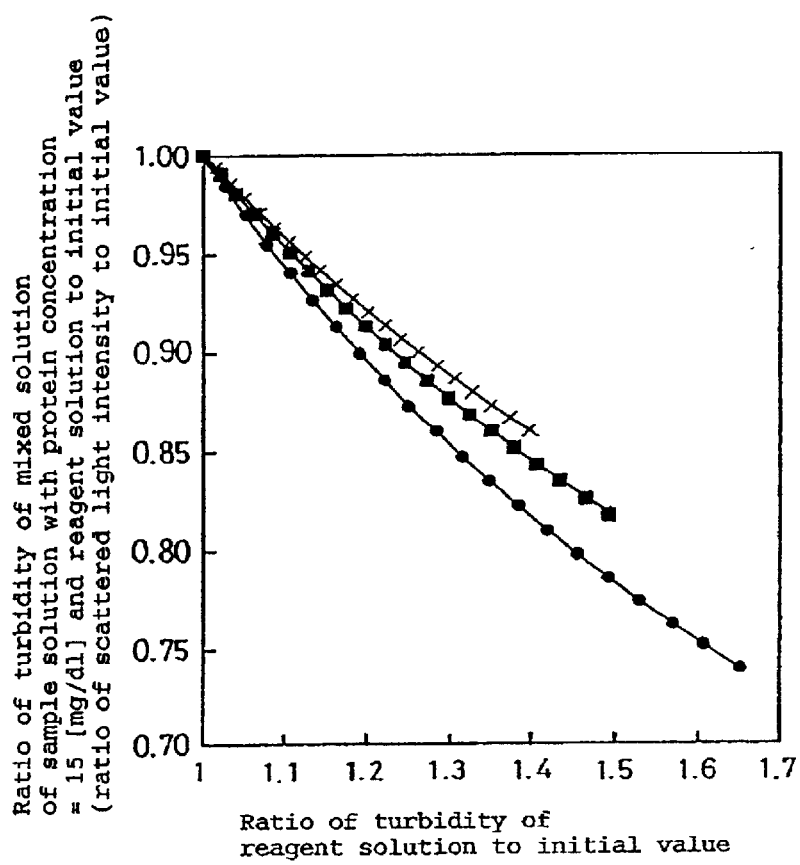
FIG. 9 shows characteristic curves each showing the relation between the turbidity of the reagent solution and the turbidity of a mixed solution containing the reagent solution and a sample solution.

(3) Step of Forming a Characteristic Curve Showing the Changes in the Optical Characteristics of a Mixed Solution with Respect to the Changes in the Optical Characteristics of a Reagent Solution Based on the Time-varying Properties A and B of Respective Optical Characteristics of the Reagent Solution and the Mixed Solution Herein, FIG. 9 showed the relation between the turbidity of a reagent solution based on FIG. 7 and the turbidity of a mixed solution containing the reagent solution and a sample solution based on FIG. 8. FIG. 9 was a graph showing the turbidities of a reagent solution and a mixed solution using the reagent solution measured on the same day. In the graph, the mark "●" indicated the relation between the turbidity of the reagent solution stored at about 0° C. and the turbidity of a mixed solution using the reagent solution; the mark "■" indicated the relation between the turbidity of the reagent solution stored at about 4° C. and the turbidity of a mixed solution using the reagent solution; and the mark "x" indicated the relation between the turbidity of the reagent solution stored at about 8° C. and the turbidity of a mixed solution using the reagent solution.

(4) Step of Examining the Characteristics of a Reagent Solution Based on the Measured Value and the Characteristic Curve Obtained by Measuring the Optical Characteristics of the Reagent Solution, Thereby Judging the Precision of the Concentration Measured Value of a Specific Component.

As apparent from FIG. 9, under the conditions in this example, the turbidity of a reagent solution was increased with a decrease in the turbidity of a mixed solution.

This indicated as follows. When the turbidity of the reagent solution was increased, the error was enlarged in calculating the concentration of a protein from the turbidity of the mixed solution, i.e., the measured value of the transmitted light intensity and/or the scattered light intensity by using FIGS. 5 and 6 as calibration lines. Accordingly, the precision of the measured value was reduced. In contrast, when the turbidity of the reagent solution was decreased, the precision of the measured value was found to be enhanced.

Further, how many times larger the turbidity of the mixed solution had become than the initial value could be predicted from the turbidity of the reagent solution at the time of measurement according to the storage environment of each reagent solution.

Therefore, when the reagent solution was under the predictable storage environment, it was possible to specify the allowable turbidity range of the reagent solution by specifying the allowable precision range of the measured value with respect to the mixed solution. Namely, when it was possible to limit the storage temperature range of the reagent solution, if the turbidity measured value of the reagent solution fell within a specified range, the turbidity measured value of the mixed solution also fell within an allowable range. Consequently, the precision could be ensured.

Further, when the turbidity of the reagent solution fell within a specified range, the measurement on the mixed solution was judged effective. Whereas, when the turbidity departed from the specified range, the measurement was judged ineffective. By this judgment of the effectiveness or the ineffectiveness, the precision of the measured value was allowed to fall within an allowable range, so that the reliability of the measurement could be ensured.

Herein, when the storage temperature range of the reagent solution was from about 0° C. to 8° C., the allowable precision range of the measured value was set within 10% (such a range that the turbidity of the mixed solution remained about 0.9 times or less the initial value). From the mark "●" of FIG. 9, when the turbidity of the reagent solution remained about 1.19 times relative to the initial value, the measurement could be judged effective. Consequently, the reliability of the measurement could be ensured.

Further, when the storage temperature range of the reagent solution was from about 0° C. to 8° C., the allowable precision range of the measured value was set within 20% (such a range that the turbidity of the mixed solution remained about 0.8 times or less the initial value). In this case, from the mark "●" of FIG. 9, when the turbidity of the reagent solution remained about 1.45 times relative to the initial value, the measurement could be judged effective. Consequently, the reliability of the measurement could be ensured.

Further, when the storage temperature range of the reagent solution was from about 4° C. to 8° C., the allowable precision range of the measured value was set within 10%. From the mark "■" of FIG. 9, when the turbidity of the reagent solution remained about 1.23 times relative to the initial value, the measurement could be judged effective.

Thus, the specified value of the turbidity of the reagent solution was set according to the storage environment of the reagent solution. Herein, by specifying the turbidity range of the reagent solution based on the characteristic curve (characteristic curve indicated by the mark "●" of FIG. 9) showing the largest changes in the turbidity of the mixed solution under a predictable storage environment, it was possible to sufficiently ensure the precision of the measured value of the mixed solution turbidity.

EXAMPLE 2

The solution concentration measuring apparatus shown in FIGS. 3 and 4 was used, and a semiconductor laser module, which projected the substantially parallel light 9 having a wavelength of 680 nm, an intensity of 15.0 mW, and a beam diameter of 2.0 mm, was used as the light source 8.

First, to a urine judged to have an albumin concentration of substantially zero (<0.01 mg/dl), was added an albumin with the respective albumin concentrations of 0, 0.2, 0.5, 1.5, 3.0, 6.0, and 10.0 mg/dl to prepare sample solutions.

Then, 1 ml of each of the sample solutions was introduced from the pipette 15 into the sample cell 10 according to the instruction from the computer 16. Then, the computer 16 operated the light source 8, and at the same time, started to monitor respective output signals from the photosensors 11 and 12.

Then, the computer 16 controlled the pipette 14, so that 1 ml of the reagent solution (a reagent solution obtained by purifying an antibody component from an antihuman rabbit serum albumin) was introduced through the inlet port 13 into the sample cell 10, and mixed with the sample solution.

Upon mixing with the reagent solution, an antigen-antibody complex was formed from the albumin (antigen) and the antibody, so that the sample solution became turbid, resulting in a reduction in the transmitted light intensity, and an increase in the scattered light intensity. The albumin concentration was measured by analyzing the changes between respective output signals from the photosensors 11 and 12 before and after the mixing of the reagent solution.

Figure 10:
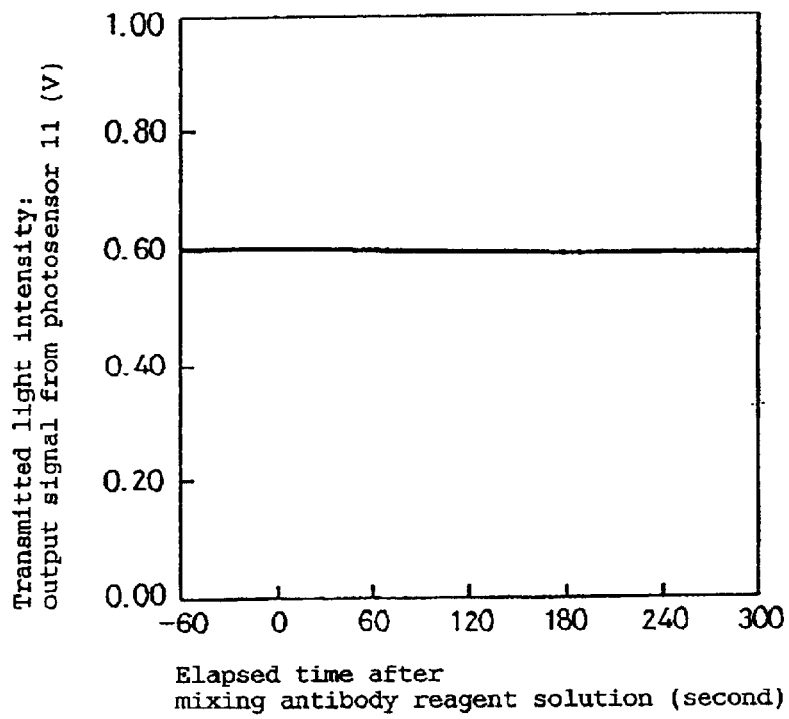
FIG. 10 is a graph showing the relation between the elapsed period after the mixing of the reagent solution and the transmitted light intensity.
Figure 11:
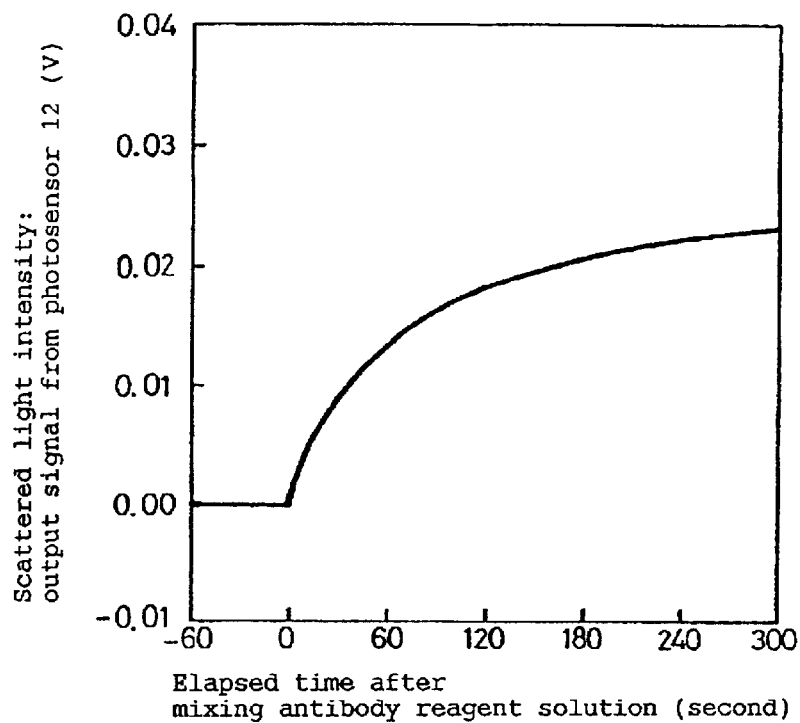
FIG. 11 is a graph showing the relation between the elapsed period after the mixing of the reagent solution and the scattered light intensity.

FIGS. 10 and 11 respectively showed the transmitted light intensity and the scattered light intensity, i.e., the output signals from the photosensors 11 and 12, when a sample solution with an albumin concentration of 0.2 mg/dl was used.

Figure 12:
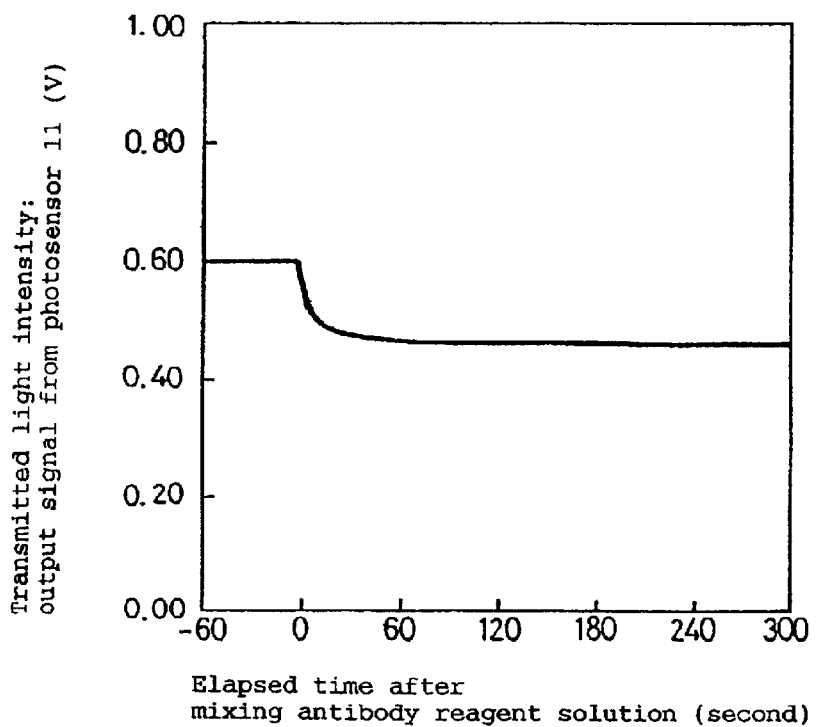
FIG. 12 is a graph showing the relation between the elapsed period after the mixing of the reagent solution and the transmitted light intensity.
Figure 13:
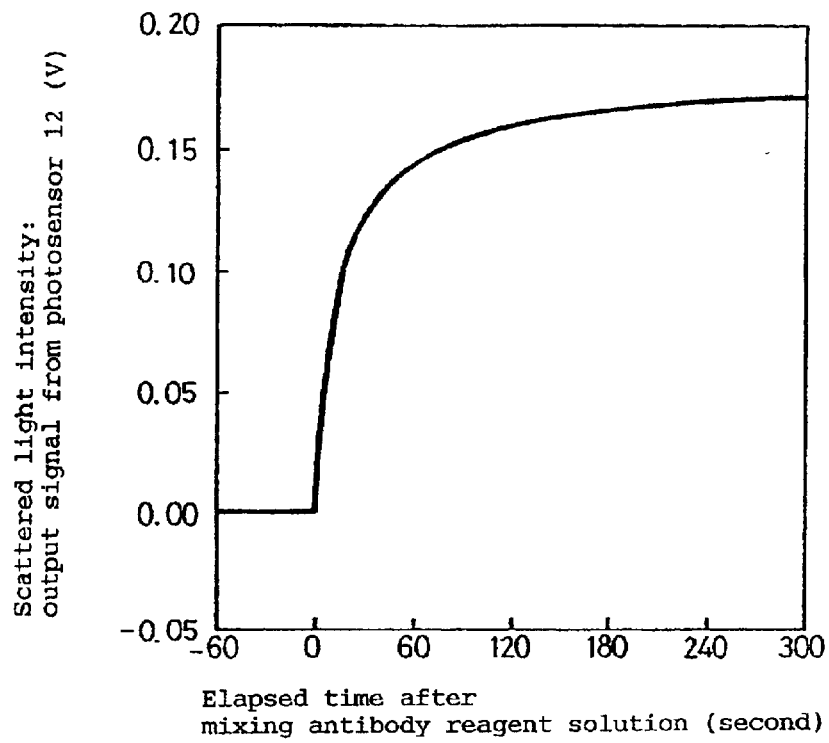
FIG. 13 is a graph showing the relation between the elapsed period after the mixing of the reagent solution and the scattered light intensity.

Similarly, FIGS. 12 and 13 respectively showed the output signals from the photosensors 11 and 12 when a sample solution with an albumin concentration of 1.5 mg/dl was used. Whereas, FIGS. 14 and 15 respectively showed the output signals from the photosensors 11 and 12 when a sample solution with an albumin concentration of 10 mg/dl was used.

In FIGS. 10 to 15, the abscissa denoted the elapsed time (second) after the mixing of the reagent solution, wherein the value with a minus sign represented the time before the mixing. Thus, each of the graphs represented the changes in the transmitted light intensity or in the scattered light intensity during a period of from 60 seconds before the mixing to 300 seconds after the mixing.

These graphs indicated that the transmitted light intensity, i.e., the output signal from the photosensor 11 was decreased in accordance with the concentration of albumin. Further, these graphs indicated that the scattered light intensity, i.e., the output signal from the photosensor 12 was increased in accordance with the concentration of albumin.

Figure 14:
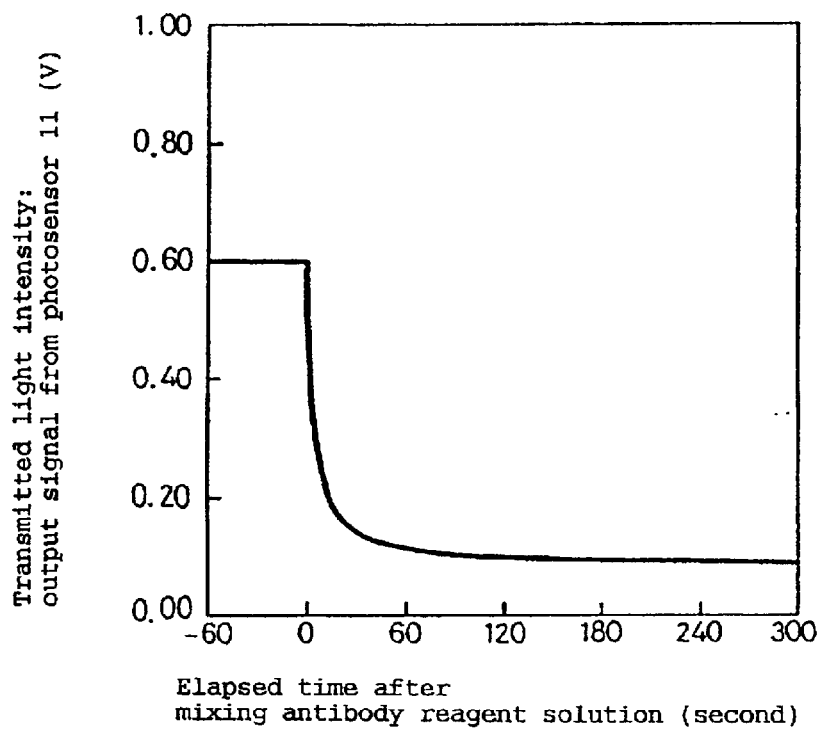
FIG. 14 is a graph showing the relation between the elapsed period after the mixing of the reagent solution and the transmitted light intensity.

Particularly, FIGS. 10, 12, and 14 indicated that the transmitted light intensity, i.e., the output signal from the photosensor 11 was decreased due to an increase in the turbidity caused by the formation of an antigen-antibody complex by albumin and an antibody thereagainst after the mixing of the reagent (after an elapse of 0 second).

Figure 15:
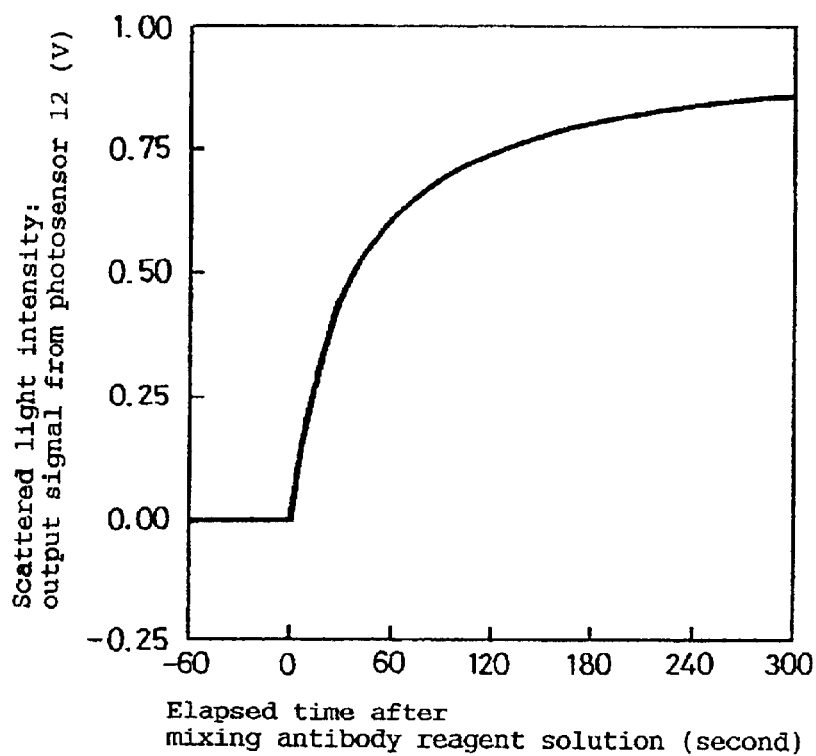
FIG. 15 is a graph showing the relation between the elapsed period after the mixing of the reagent solution and the scattered light intensity.

Further, FIGS. 11, 13, and 15 indicated that the scattered light intensity, i.e., the output signal from the photosensor 12 was increased due to an increase in the turbidity caused by the formation of an antigen-antibody complex by albumin and an antibody thereagainst.

Figure 16:
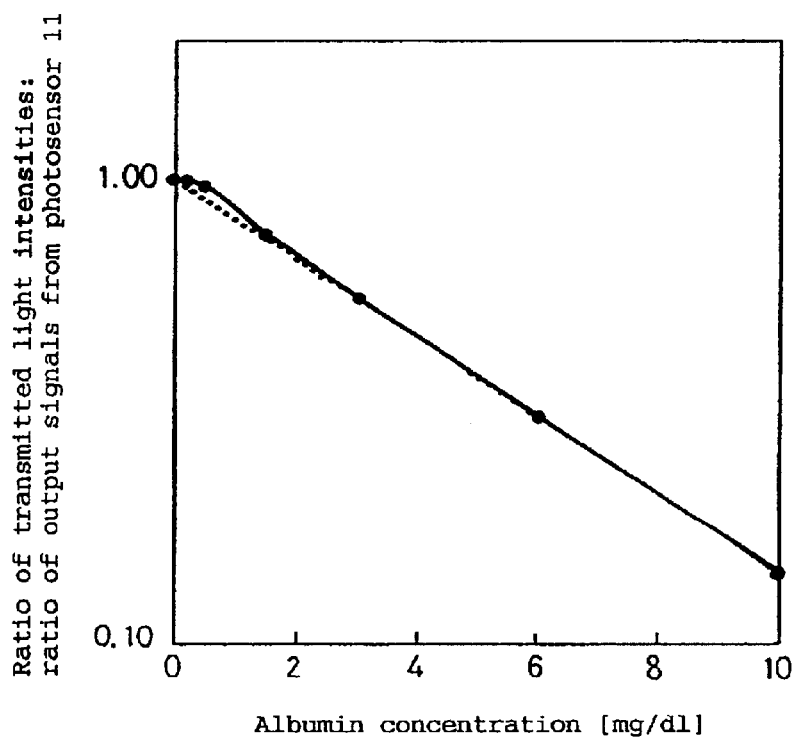
FIG. 16 is a graph showing the relation between the transmitted light intensity and the albumin concentration.
Figure 17:
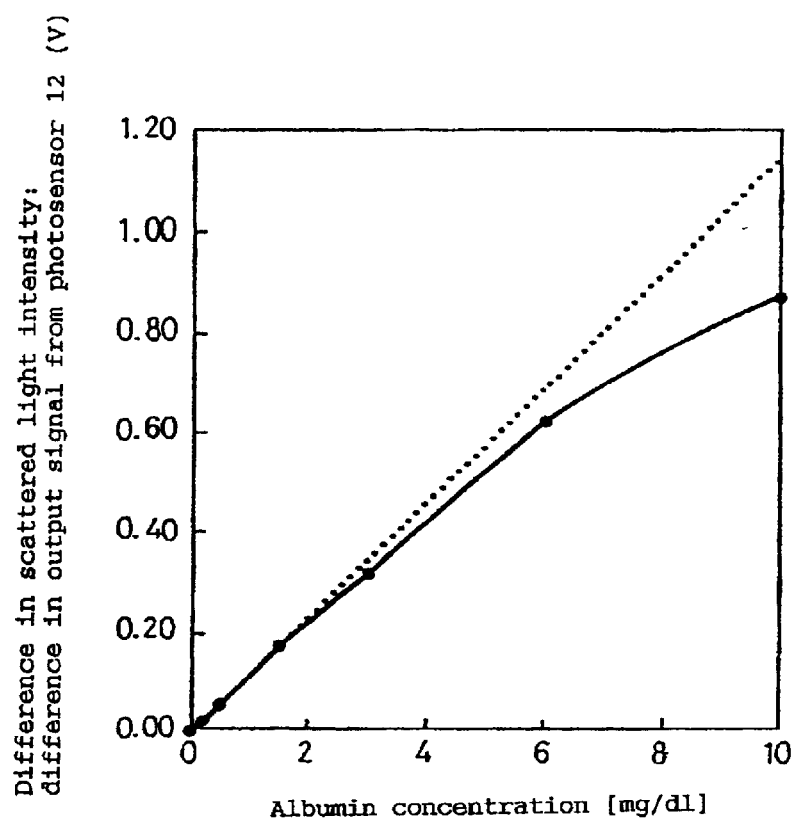
FIG. 17 is a graph showing the relation between the scattered light intensity and the albumin concentration.

FIGS. 16 and 17 showed the relation between the transmitted light and the albumin concentration, and the relation between the scattered light intensity and the albumin concentration, respectively.

In FIG. 16, the ordinate denoted the ratio between the transmitted light intensity at the time of mixing the reagent (0 second), and the transmitted light intensity after an elapse of 300 seconds from the mixing. In FIG. 17, the ordinate denoted the difference between the scattered light intensity at the time of mixing the reagent (0 second), and the scattered light intensity after an elapse of 300 seconds from the mixing. These graphs could be used as calibration lines in the concentration measurement.

The sample solution and the reagent solution, measured herein, had almost the same transparency as that of pure water so long as they were under the conditions under which the calibration lines of FIGS. 10 to 15 had been formed by using the apparatus shown in FIGS. 3 and 4. Namely, the transmitted light intensity and the scattered light intensity of the sample solution (output signals from the photosensors 11 and 12) before the mixing of the reagent solution were almost the same as the transmitted light intensity and scattered light intensity of pure water. Further, the transmitted light intensity and the scattered light intensity when only the reagent solution was charged into the sample cell 10 were almost the same as those of pure water, similarly.

In FIG. 16, the abscissa denoted the albumin concentration, and the ordinate (logarithmic scale) denoted the ratio of the transmitted light intensities. Respective points were smoothly connected to obtain a solid line, and the points showing linearly changing values at concentrations of 1.5, 3, 6, and 10 mg/dl were linearly connected to obtain a dotted line.

As shown in FIG. 16, at concentrations of 0.2 and 0.5 mg/dl, the measured value might deviate from the dotted line. The reason for this was as follows: as apparent from the comparison among FIGS. 10, 12, and 14, since the amount of change, i.e., the ratio of change was too small as compared with all the output signals, the measured value was susceptible to various noises in association with the dynamic range.

For these reasons, a high concentration region of 1.5 mg/dl or more was desirable in order to avoid the influences of various noises when the concentration was calculated from the transmitted light intensity.

In FIG. 17, the abscissa denoted the albumin concentration, and the ordinate denoted the amount of changes in the scattered light intensities. Respective points were smoothly connected to obtain a solid line, and the points showing linearly changing values at concentrations of 0, 0.2, 0.5, and 1.5 mg/dl were linearly connected to obtain a dotted line.

As apparent from the solid line and the dotted line, the scattered light intensity was proportional to the concentration at concentrations of up to about 1.5 mg/dl. However, as the concentration increased more than the value in the vicinity of this range, the gradient was gradually decreased.

The reason for this was as follows. When the probability that light was scattered was increased with an increase in the concentration, the probability that light was scattered again was also increased during propagation of light from the point where the scattered light has arisen to the outside of the sample cell, resulting in a reduction in the probability that the scattered light reached the photosensor 12. Therefore, when the concentration was calculated from the scattered light intensity, the linearity could be ensured only in the low concentration region (about 15 mg/dl or less).

For the low concentration region, the concentration was calculated from the changes in the scattered light intensity. Whereas, for the high concentration region, the concentration was calculated from the changes in the transmitted light intensity. Consequently, it was possible to substantially enlarge the concentration range measurable with high precision. Specifically, when the ratio of changes in the transmitted light intensity was 0.7 or less, the concentration was calculated by using the graph of FIG. 16 as a calibration line. Whereas, when the scattered light intensity was about 0.2 V or less, the concentration was calculated by using the graph of FIG. 17 as a calibration line.

Next, in the method in accordance with the present invention, the optical characteristic of the reagent solution itself was measured in the following manner. The precision of the measured value of the concentration was judged by using the measured value.

(1) Step of Determining the Time-varying Property A of the Optical Characteristics of a Reagent Solution at Respective Time Points of Storage Under a Specific Storage Environment First, an antibody reagent solution was prepared in the same manner as described above.

Subsequently, only the reagent solution was charged in an amount of 2 ml into the sample cell 10 of the solution concentration measuring apparatus shown in FIGS. 3 and 4 to measure the turbidity. At this step, the output signal from the photosensor 12 was enlarged (amplified) to 100 times the signal when the calibration lines shown in FIGS. 11, 13, and 15 had been formed, and observed by the computer 16.

Then, the turbidity of the reagent solution was measured every 30 days from immediately after the preparation of the reagent solution to 600th days therefrom.

Figure 18:
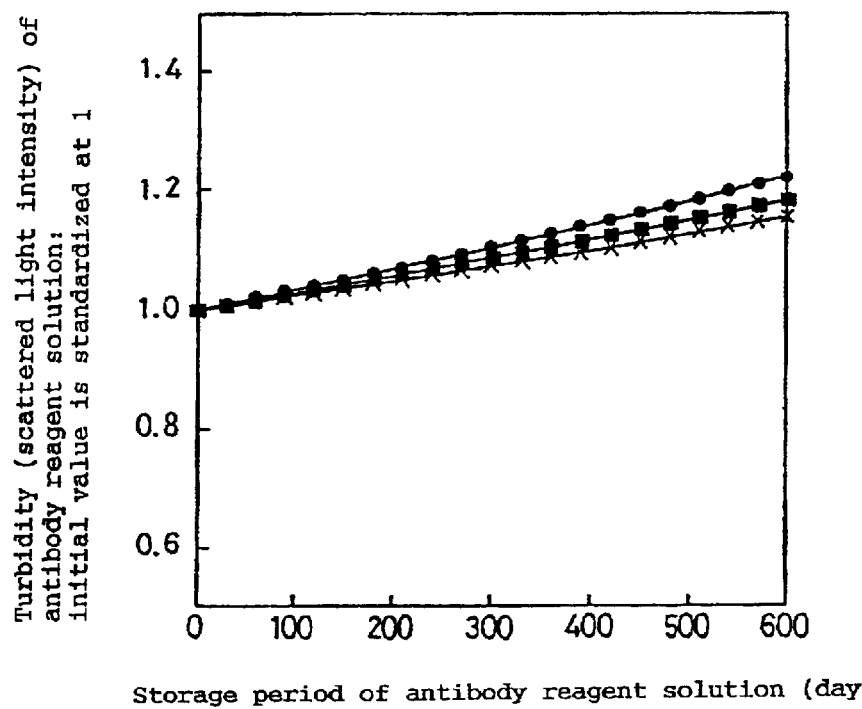
FIG. 18 shows calibration lines each showing the relation between the storage period of the reagent solution and the scattered light intensity of the reagent solution at each time point of storage.

The result, i.e., the time-varying property A, was shown in FIG. 18. In FIG. 18, the abscissa denoted the storage period (the number of days elapsed from immediately after the preparation) of the reagent solution. Whereas, the ordinate denoted the scattered light intensity at each time point when the scattered light intensity (output signal from the photosensor 12) immediately after the preparation was assumed to be an initial value. Namely, the initial value was assumed to be 1, and the subsequent scattered light intensities were indicated by indexes. Then, respective points were smoothly connected by a solid line.

In FIG. 18, the mark "●" indicated the case where the reagent solution stored at about 50° C. was used; the mark "■" indicated the case where the reagent solution stored at about 45° C. was used; and the mark "x" indicated the case where the reagent solution stored at about 40° C. was used. However, in any case, the temperature was lowered to room temperature (about 20° C.) for measuring the turbidity.

(2) Step of Measuring the Optical Characteristics of a Mixed Solution at Respective Time Point of Storage, and Determining the Time-varying Property B of the Optical Characteristics of the Mixed Solution Whereas, the scattered light intensity (amount of changes in output signal from the photosensor 12) of a sample solution having an albumin concentration of 1.5 mg/dl was measured by using the reagent solution under the same conditions and settings as those for forming the calibration lines shown in FIGS. 11 and 17.

Namely, the reagent solution after each storage was injected by the pipette 14 into the fresh sample solution in the sample cell 10 as described above every 30 days from immediately after the preparation of the reagent solution to 600th days therefrom, and was mixed with the sample solution. Thus, the turbidity, i.e., the scattered light intensity of the resulting mixed solution was measured. However, the sample solution had been prepared immediately before each measurement, and hence no consideration was given to the change in the characteristics of the sample solution itself.

Figure 19:
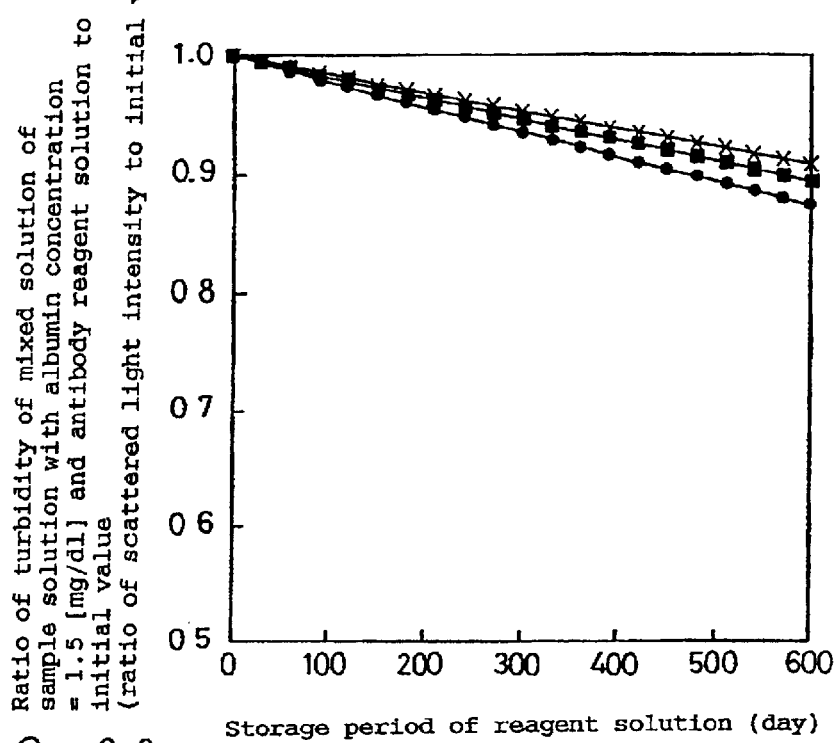
FIG. 19 shows calibration lines each showing the relation between the storage period of the reagent solution and the scattered light intensity of a mixed solution using the reagent solution at each time point of storage.

The result, i.e., the time-varying property B, was shown in FIG. 19. In FIG. 19, the abscissa denoted the storage period (the number of days elapsed from immediately after the preparation) of the reagent solution. Whereas, the ordinate denoted the ratio between the scattered light intensity of the mixed solution using the reagent solution after storage and the scattered light intensity of the mixed solution using the reagent solution immediately after the manufacturing thereof. Namely, the ordinate denoted the scattered light intensity at each time point on the assumption that the scattered light intensity (output signal from the photosensor 5) of the mixed solution using the reagent solution immediately after the preparation was an initial value. The initial value was assumed to be 1, and the subsequent measured values were indicated by indexes. Then, respective points were smoothly connected by a solid line.

FIG. 19, the mark "●" indicated the turbidity of the mixed solution using the reagent solution stored at about 50° C.; the mark "■" indicated the turbidity of the mixed solution using the reagent solution stored at about 45° C.; and the mark "x" indicated the turbidity of the mixed solution using the reagent solution stored at about 40° C. However, in any case, the temperature was lowered to room temperature (about 20° C.) for measuring the turbidity.

As apparent from FIG. 18, the turbidity of the reagent solution was increased with an increase in the storage period. For example, the scattered light intensity of the reagent solution stored at about 50° C. indicated by the mark "●" was about 1.1 times the initial value after an elapse of 300 days, and about 1.22 times the initial value after an elapse of 600 days.

Whereas, as apparent from FIG. 19, the turbidity of the mixed solution of the sample solution and the antibody reagent solution was decreased with an increase in the storage period. For example, the scattered light intensity of the mixed solution using the reagent solution stored at about 50° C. indicated by the mark "●" was about 0.94 times the initial value after an elapse of 300 days, and about 0.88 times the initial value after an elapse of 600 days.

Figure 20:
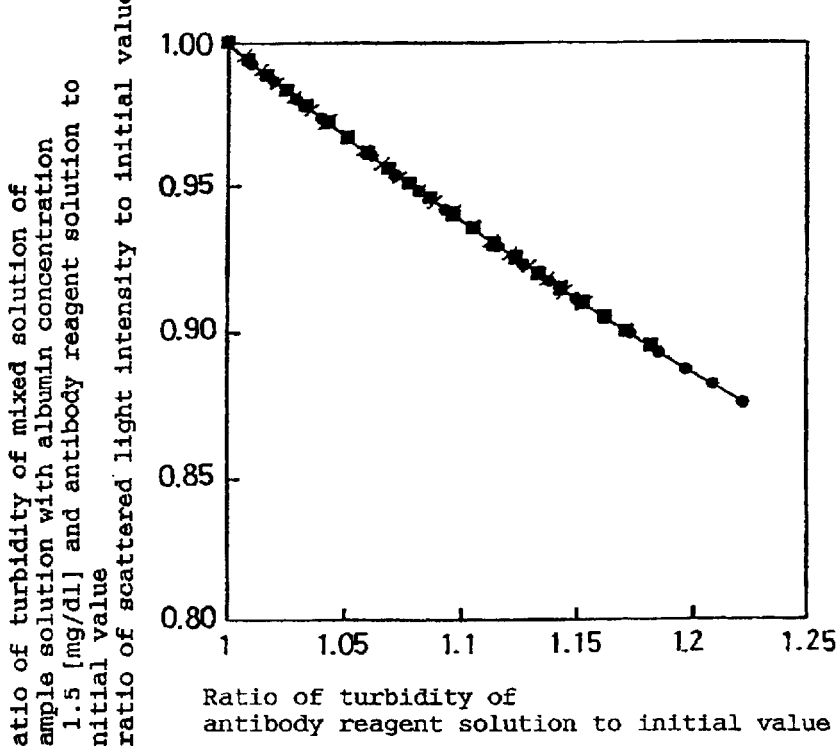
FIG. 20 shows a characteristic curve showing the relation between the turbidity of the reagent solution and the turbidity of a mixed solution containing the reagent solution and a sample solution.

3) Step of Forming a Characteristic Curve Showing the Changes in the Optical Characteristics of the Mixed Solution with Respect to the Changes in the Optical Characteristics of the Reagent Solution Based on the Time-varying Properties A and B of Respective Optical Characteristics of the Reagent Solution and the Mixed Solution Herein, FIG. 20 showed a characteristic curve showing the relation between the turbidity of a reagent solution based on FIG. 18 and the turbidity of a mixed solution containing the reagent solution and a sample solution based on FIG. 19. FIG. 20 was a graph showing the turbidities of a reagent solution and a mixed solution using the reagent solution measured on the same day. In the graph, the mark "●" indicated the relation between the turbidity of the reagent solution stored at about 50° C. and the turbidity of a mixed solution using the reagent solution; the mark "■" indicated the relation between the turbidity of the reagent solution stored at about 45° C. and the turbidity of a mixed solution using the reagent solution; and the mark "x" indicated the relation between the turbidity of the reagent solution stored at about 40° C. and the turbidity of a mixed solution using the reagent solution.

(4) Step of Examining the Characteristics of a Reagent Solution Based on the Measured Value and the Characteristic Curve Obtained by Measuring the Optical Characteristics of the Reagent Solution, Thereby Judging the Precision of the Concentration Measured Value of a Specific Component.

As apparent from FIG. 20, under the conditions in this example, the turbidity of a reagent solution was increased with a decrease in the turbidity of a mixed solution.

This indicated as follows. When the turbidity of the reagent solution was increased, the error was enlarged in calculating the concentration of albumin from the turbidity of the mixed solution, i.e., the difference in the transmitted light intensity and/or the scattered light intensity by using FIGS. 16 and 17 as calibration lines. Accordingly, the precision of the measured value was reduced. In contrast, when the turbidity of the reagent solution was decreased, the precision of the measured value was found to be enhanced.

As apparent from the comparison between FIG. 20 and FIG. 7, the difference between calibration lines each showing the relation between the turbidity of a reagent solution and the turbidity of a mixed solution, caused by the difference in the storage environment (storage temperature) between the reagent solutions was not substantially observed in this example. However, it was possible to predict how many times larger than the initial value the turbidity of the mixed solution had become based on the turbidity of the reagent solution at the time of measurement.

Therefore, when the reagent solution was under the predictable storage environment, it was possible to specify the allowable turbidity range of the reagent solution by specifying the allowable precision range of the measured value with respect to the mixed solution. Namely, when it was possible to limit the storage temperature range of the reagent solution, if the measured value of the turbidity of the reagent solution fell within a specified range, the measured value of the turbidity of the mixed solution also fell within an allowable range. Consequently, the precision could be ensured.

Further, when the turbidity of the reagent solution falls within a specified range, the measurement on the mixed solution was judged effective. Whereas, when it departed from the specified range, it was judged ineffective. By this judgment of the effectiveness or the ineffectiveness, the precision of the measured value was allowed to fall within an allowable range, so that the reliability of the measurement could be ensured.

Herein, when the storage temperature range of the reagent solution was from about 40° C. to 50° C., the allowable precision range of the measured value was set within 5% (such a range that the turbidity of the mixed solution remained about 0.95 times or less the initial value). From the marks "●", "■", and "x" of FIG. 20, when the turbidity of the reagent solution remained about 1.08 times relative to the initial value, the measurement could be judged effective. Consequently, the reliability of the measurement could be ensured.

Whereas, when the storage temperature range of the reagent solution was from about 0° C. to 8° C., the allowable precision range of the measured value was set within 10% (such a range that the turbidity of the mixed solution remained about 0.9 times or less the initial value). From the marks "●", "■", and "x" of FIG. 20, when the turbidity of the reagent solution remained about 1.17 times to the initial value, the measurement could be judged effective. Consequently, the reliability of the measurement could be ensured.

In the case of this example, so long as the storage temperature of the reagent solution was in the range of from about 40° C. to 50° C., by setting the specified value of the turbidity of the reagent solution irrespective of the storage environment of the reagent solution, it was possible to allow the precision of the measured value to fall within an allowable range.

EXAMPLE 3

In this example, the protein concentration was measured by using the solution concentration measuring apparatus shown in FIGS. 1 and 2. Further, by using a biuret reagent (a reagent obtained by dissolving potassium sodium tartrate and copper sulfate in a sodium hydroxide solution) as a reagent solution, the absorbance of the reagent solution was calculated from the transmitted light intensity, i.e., the output signal from the photosensor 4 by using the solution concentration measuring apparatus shown in FIGS. 1 and 2. The absorbance used was the absorbance with respect to a wavelength=780 nm.

Then, the same protein-containing urine (sample solution) as that of Example 1 was prepared, and mixed with the reagent solution to obtain a mixed solution. The absorbance with respect to a wavelength=546 nm was measured for the mixed solution by using a conventional spectrometer. Herein, a conventional rectangular sample cell with an optical path length of 10 mm was used. The protein concentration was calculated from the absorbance with respect to a wavelength=546 nm.

The absorbance immediately after the preparation of the reagent solution was about 0.35 (about 45% in transmittance, optical path length=10 mm) with respect to a wavelength of 780 nm. The reagent solution in this state was mixed with the sample solution, and the absorbance of the mixed solution was measured to form the calibration line shown in FIG. 21. In FIG. 21, the abscissa denoted the concentration of protein in the urine, and the ordinate denoted the absorbance of the mixed solution. It was possible to calculate the protein concentration by using the calibration line.

Simulating the changes comparable to those in an atmosphere, the reagent solution was stored in a thermostat changing in temperature in the range of from −10° C. to 40° C. in a cycle of 24 hours. Upon an elapse of 200 days, the absorbance was about 0.4 (about 40% in transmittance, optical path length=10 mm).

Under the same conditions under which the calibration line of FIG. 21 had been formed, the reagent solution was mixed with the sample solution to obtain a mixed solution. The absorbance of the mixed solution was measured, and in some cases, the measured value significantly deviated from the calibration line of FIG. 21. Further, the reproducibility of the measured value was also poor.

For example, the absorbance when the protein concentration=100 mg/dl was about 0.08 in FIG. 21. Whereas, some mixed solutions using the reagent solution exhibited an absorbance of 0.1 or more. Further, the absorbance showed a large difference from one measurement to another, and the reproducibility was poor.

As apparent from the foregoing description, when the absorbance of the reagent solution at 780 nm was increased, the measurement precision was decreased. Therefore, by calculating the characteristic (the absorbance herein) of the reagent solution in the same manner as in Examples 1 and 2, it was possible to judge the precision of the measurement using the reagent solution from the measured value.

Then, for example, when the absorbance of the reagent solution at 780 nm was 0.4 or more, the measurement using the reagent solution was judged ineffective, so that it was possible to ensure the reliability of the measurement.

Further, as in this example, when the overview of the time-varying properties of the optical characteristics of the reagent solution and the mixed solution was obscure, by judging the measurement using the reagent solution to be ineffective at the time of detecting the changes in the optical characteristics of the reagent solution, it was possible to ensure the reliability of the measurement.

As described above, according to this example, when the concentration of a specific component in a sample solution was measured, the optical characteristics of a reagent solution was also measured. Based on this measured value, the precision of the measured value of the concentration of the specific component was judged. Accordingly, it was possible to judge whether the measurement was effective or ineffective from this judgment result, so that it was possible to ensure the reliability of the measurement.

As described above, the present invention is based on the phenomenon that when the optical characteristics of a reagent solution is changed, the optical characteristic of a mixed solution using the same is also changed. Simultaneously, the present invention is based on the following founding. Namely, by ascertaining the relation between the changes in the optical characteristics of the reagent solution and the changes in the optical characteristics of the mixed solution (corresponding to a characteristic curve), and measuring the optical characteristics of the reagent solution based on this relation, it is possible to judge the precision of the measurement of the optical characteristics of the mixed solution.

Further, in certain conditions, the optical characteristics of the mixed solution are not changed unless the optical characteristics of the reagent solution are changed. Therefore, the optical characteristics of the mixed solution are changed at the time when the changes in the optical characteristics of the reagent solution has been detected, so that it is possible to judge that the precision might be reduced.

As described above, according to the present invention, when the concentration of a specific component in a sample solution is measured, the optical characteristic of a reagent solution is also measured. Then, based on this measured value, the precision of the measured value of the concentration of the specific component can be judged. Accordingly, it is possible to judge whether the measurement is effective or ineffective from this judgment result, thereby ensuring the reliability of the solution concentration measurement with simplicity and ease.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method for measuring an optical characteristic of a mixed solution of a sample solution and a reagent solution, said method comprising the steps of:
   (1) previously determining a time-varying property A of the optical characteristic of said reagent solution at multiple time points of storage under a specific storage environment;
   (2) measuring an optical characteristic of a mixed solution of said sample solution and said reagent solution at said multiple time points of storage to determine a time-varying property B of the optical characteristic of said mixed solution; and
   (3) determining a characteristic curve showing changes in said optical characteristic of the mixed solution with respect to changes in said optical characteristic of the reagent solution based on said time-varying properties A and B.

2. The method in accordance with claim 1, wherein the step (3) includes a step of examining a characteristic of said reagent solution based on said characteristic curve and a measured value obtained by measuring said optical characteristic of the reagent solution.

3. The method in accordance with claim 2, wherein said optical characteristic of the mixed solution to be measured is an absorbance or a turbidity.

4. The method in accordance with claim 3, wherein said optical characteristic of the reagent solution to be measured is an absorbance or a turbidity.

5. The method in accordance with claim 4, wherein said optical characteristics of the mixed solution and the reagent solution to be measured are the same, and measured by using a light having the same wavelength.

6. The method in accordance with claim 4, wherein said optical characteristics of the mixed solution and the reagent solution to be measured are the same, and measured by means of the same optical characteristic measuring apparatus.

7. The method in accordance with claim 4, wherein the precision of a measured value of the concentration of a specific component is judged to be low when said turbidity of the reagent solution is high or low, and the precision of a measured value of the concentration of a specific component is judged to be high when said turbidity of the reagent solution is low or high.

8. The method in accordance with claim 4, wherein the precision of a measured value of the concentration of a specific component is judged to be high and effective when said turbidity of the reagent solution is not more than or not less than a predetermined value.

9. The method in accordance with claim 4, wherein the precision of a measured value of the concentration of a specific component is judged by taking an absorbance and/or a turbidity of the reagent solution to be used in a first round of a solution concentration measuring method immediately after manufacturing thereof as an initial value, and comparing an absorbance and/or a turbidity of the reagent solution to be used in a second or later round of a solution concentration measuring method is compared with the initial value.

10. The method in accordance with claim 9, wherein a measured value of the concentration of a specific component is judged to be effective when the difference and/or the ratio between said absorbance and/or said turbidity in the second or later round and said initial value is not more than a predetermined value.

11. A solution concentration measuring apparatus comprising: a light source for irradiating a sample solution containing a specific component with a light; a sample cell for holding said sample solution such that a light transmits through said sample solution; a photosensor 1 for detecting said light transmitted through the sample solution and/or a photosensor 2 disposed so as to detect a scattered light arisen when said light propagates through the inside of said sample solution; a transfusion system for introducing said sample solution and a reagent solution into said sample cell; and a computer for controlling said transfusion system to analyze an output signal from said photosensor 1 and/or said photosensor 2,
   wherein said computer comprises: a memory unit for storing a time-varying property A of an optical characteristic of said reagent solution previously determined at multiple time points of storage under a specific storage environment; a control unit for using an output signal from said photosensor 1 and/or said photosensor 2 as a measured value corresponding to an optical characteristic, and measuring an optical characteristic of a mixed solution of said sample solution and said reagent solution at said multiple time points of storage to determine a time-varying property B of an optical characteristic of said mixed solution; a comparison unit for determining a characteristic curve showing changes in said optical characteristic of the mixed solution with respect to changes in said optical characteristic of the reagent solution based on said time-varying properties A and B; and a display unit for displaying a result of the comparison unit.

12. The solution concentration measuring apparatus in accordance with claim 11, wherein said control unit calculates said concentration of the specific component of the sample solution by using an output signal from said photosensor 2 as a measured value corresponding to said optical characteristic when the concentration of the sample solution with a low concentration of the specific component is determined, and using an output signal from said photosensor 1 as a measured value corresponding to said optical characteristic when the concentration of the sample solution with a high concentration of the specific component is determined, thereby to enlarge a measurable concentration range.

13. The solution concentration measuring apparatus in accordance with claim 12, wherein said control unit improves a characteristic examination precision of said reagent solution by using an output signal from said photosensor 2 as a measured value corresponding to said optical characteristic of the reagent solution.

* * * * *